(12) United States Patent
Kim

(10) Patent No.: US 9,144,289 B2
(45) Date of Patent: Sep. 29, 2015

(54) WRINKLE-REMOVING TAPE

(76) Inventor: Yong Jin Kim, Goyang-si (KR)

( * ) Notice: Subject to any disclaimer, the term of this patent is extended or adjusted under 35 U.S.C. 154(b) by 45 days.

(21) Appl. No.: 13/387,746

(22) PCT Filed: Aug. 7, 2010

(86) PCT No.: PCT/KR2010/005189
§ 371 (c)(1),
(2), (4) Date: Jan. 30, 2012

(87) PCT Pub. No.: WO2011/019169
PCT Pub. Date: Feb. 17, 2011

(65) Prior Publication Data
US 2012/0143240 A1    Jun. 7, 2012

(30) Foreign Application Priority Data

Aug. 8, 2009  (KR) .................. 10-2009-0073051
Aug. 7, 2010  (KR) .................. 10-2010-0076149

(51) Int. Cl.
| | |
|---|---|
| *A61F 5/08* | (2006.01) |
| *A45D 44/22* | (2006.01) |
| *A45D 34/04* | (2006.01) |
| *A61B 17/32* | (2006.01) |
| *A61B 17/00* | (2006.01) |
| *A61B 17/34* | (2006.01) |

(52) U.S. Cl.
CPC ............... *A45D 44/22* (2013.01); *A45D 34/04* (2013.01); *A61B 17/32* (2013.01); *A45D 2200/1009* (2013.01); *A61B 2017/00761* (2013.01); *A61B 2017/00942* (2013.01); *A61B 2017/320004* (2013.01); *A61B 2017/3437* (2013.01)

(58) Field of Classification Search
CPC .................. A45D 34/04; A45D 44/22; A45D 2200/1009; A61B 17/32; A61B 2017/3437; A61B 2017/00761; A61B 2017/00942; A61B 2017/320004; A61B 17/132; A61F 2013/530481; A61F 13/53
USPC .................... 606/204.35, 201, 202, 203, 204; 602/54, 55, 56; 604/372
See application file for complete search history.

(56) References Cited

U.S. PATENT DOCUMENTS

| | | | | |
|---|---|---|---|---|
| 4,055,180 | A | * | 10/1977 | Karami .................... 604/368 |
| 5,454,800 | A | * | 10/1995 | Hirt et al. ................ 604/378 |
| 5,788,684 | A | * | 8/1998 | Abuto et al. ............. 604/368 |

(Continued)

FOREIGN PATENT DOCUMENTS

| | | |
|---|---|---|
| JP | 2003-520063 A | 7/2003 |
| JP | 2005-124916 A | 5/2005 |

(Continued)

*Primary Examiner* — Katrina Stransky
(74) *Attorney, Agent, or Firm* — IM IP Law PLLC; C. Andrew Im

(57) ABSTRACT

The present invention relates to a wrinkle-removing apparatus. When the wrinkle removing apparatus of the present invention adopting a vacuum suction system is tightly applied to the shallow wrinkles on a forehead or to deep wrinkles, a vacuum is created by means of the elasticity of the wrinkle-removing apparatus, in order to strongly suck and pull wrinkles outwardly from the skin. Repeated use of the apparatus with the above-described condition enables a substance such as subcutaneous fat or collagen to replace the wrinkles at the back surface of the wrinkled skin when wrinkles are pulled outwardly from the skin, and finally, skin wrinkles are removed even when the apparatus is no longer used.

18 Claims, 5 Drawing Sheets

(56) References Cited

U.S. PATENT DOCUMENTS

| | | | |
|---|---|---|---|
| 6,566,575 B1* | 5/2003 | Stickels et al. | 602/41 |
| 2004/0127839 A1* | 7/2004 | Sigurjonsson et al. | 602/55 |
| 2004/0138604 A1* | 7/2004 | Sigurjonsson et al. | 602/48 |
| 2006/0182787 A1* | 8/2006 | Jaenichen et al. | 424/445 |
| 2008/0234645 A1* | 9/2008 | Dodge et al. | 604/368 |

FOREIGN PATENT DOCUMENTS

| | | |
|---|---|---|
| JP | 2006-043255 A | 2/2006 |
| JP | 2006-149444 A | 6/2006 |

* cited by examiner

WRINKLE-REMOVING TAPE

CROSS-REFERENCES TO RELATED APPLICATIONS

The present application is a §371 national stage application from International Application PCT/KR2010/005189, with an International Filing Date of Aug. 7, 2010, which claims priority from Korean Patent Application Nos. 10-2009-0073051 filed Aug. 8, 2009 and 10-2010-0076149 filed Aug. 7, 2010, each of which is incorporated herein by reference in its entirety.

FIELD OF THE INVENTION

The present invention relates to a tape for removing wrinkles Typically, wrinkles correspond to a phenomenon in which an adhesion surface between the epidermis and the dermis of the skin is wrinkled as the adhesion surface is reduced. The wrinkles are generated when the collagen fiber and resilient fiber of the dermis are broken and cells and capillary vessels at a boundary of the epidermis and the dermis are reduced. A cause of skin aging may chiefly include two kinds; age aging and sunlight aging. Age aging refers to aging according to a lapse of time which is indispensable as a person grows old. Sunlight aging means aging resulting from a ray of light, in particular, ultraviolet rays. It has been known that fine wrinkles formed by this aging are generated when the degree of finer elasticity is changed according to a reduction in the amount of collagen in the dermis layer of the skin and consequently the skin is extended and deep wrinkles are generated by an excessive action of muscle below the skin. There have been made to a lot of efforts to remove the wrinkles.

BACKGROUND OF THE RELATED ART

Several methods are being attempted to remove the wrinkles in numerous cosmetic centers. From among the methods, commercialized technology is a method of injecting collagen or BOTOX® (a registered trademark of Allergan, Inc.) into a portion under the wrinkles. This method is the most effective method of smoothing out the wrinkles. A variety of methods, such as a massage, are being attempted.

SUMMARY OF THE INVENTION

An object of the present invention is to remove wrinkles by providing a construction which can be precisely adhered to and adsorbed by wrinkles and closely adhered to the epidermis in an air-tight manner for a long time so that the construction is not detached from the skin.

To achieve the above object, according to the present invention, a lot of very small and fine partitions are formed in one face of the top of tape means, the partitions are filled with a high-suction polymer substance, water-flow non-woven fabric or a fine perforation resin film is adhered to the top thereof, adhesion means capable of being adhered to the skin is uniformly sprayed at the bottom of tape means, thereby forming an adhesion surface, and a rear paper for protecting the adhesion surface is adhered in a tape form.

As described above, the wrinkle-removing tape of the present invention is properly cut and adhered to a wrinkled portion after the rear paper is peeled off. When moisture on the skin is absorbed by the high suction polymer substance of the tape along the wrinkles using felt-tip pen type moisture discharge means, a skin portion in which the moisture is absorbed rises quickly by means of force expanded as the polymer absorbs moisture, thereby smoothing out the wrinkles. The wrinkles can be effectively smoothed out for a long time by accurately pulling only the wrinkled skin. If the tape is repeatedly used, a significant effect can be achieved.

BRIEF DESCRIPTION OF THE DRAWINGS

Further objects and advantages of the invention can be more fully understood from the following detailed description taken in conjunction with the accompanying drawings in which.

DETAILED DESCRIPTION OF EMBODIMENTS

A construction and embodiment of the present invention are described with reference to the accompanying drawings.

Figure 1:
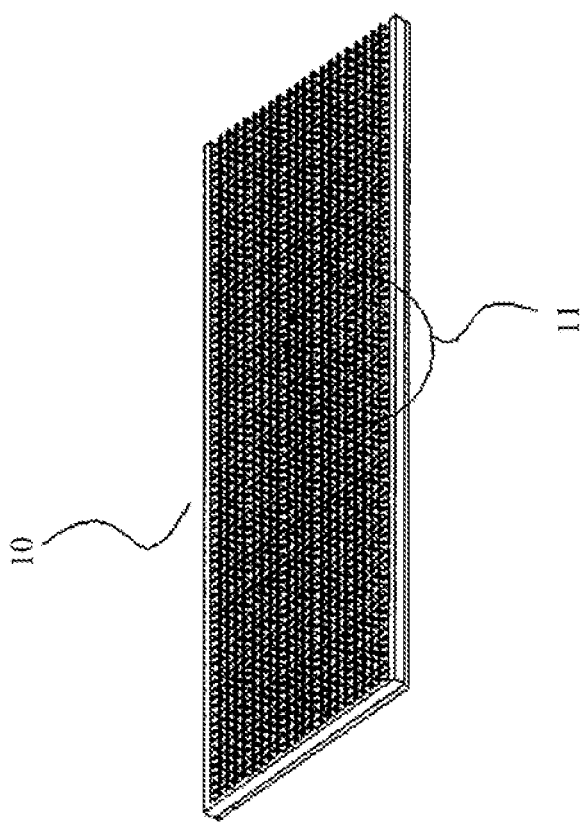
FIG. 1 is a perspective view of partition tape means 10.
Figure 2:
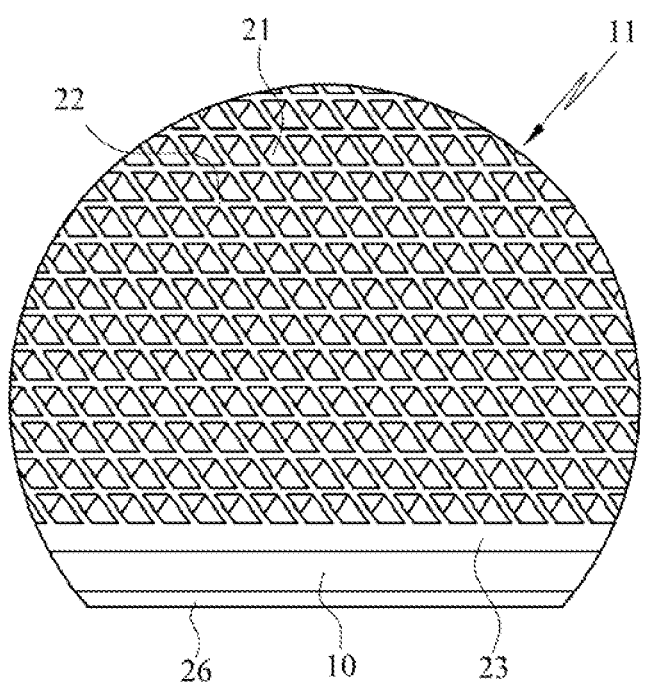
FIG. 2 is an enlarged view of a portion 11 in FIG. 1.

Partition tape means 10 shown in FIGS. 1 and 2 includes an adhesion surface and adhesion means on its lower side, a rear paper 26 adhered thereto so that it can be peeled off in order to prevent the adhesion means from being contaminated, fine hole partition means 21 on its top surface, and partitions 22 outside the fine hole partition means 21. In the present invention, the fine hole partition means 21 and the partitions 22 are illustrated in a square form because the fine hole partition means 21 must be densely formed, but the fine hole partition means 21 and the partitions 22 may be formed in a hexagonal form of a beehive form. If the fine hole partition means 21 is formed in a circular form, however, there is a disadvantage in that the area of the fine hole partition means 21 is relatively reduced because a space occupied by the partitions 22 is increased.

For this reason, in the wrinkle-removing tape of the present invention, the fine hole partition means 21 may be fabricated in a polygonal form, including a square or hexagon, and may also be fabricated in a circular form.

An edge blank portion 23 is formed slightly widely at the end of the partition tape means 10 in its width direction. The adhesion means is coated on the top of the blank portion 23 and the partitions 22, and water-flow non-woven fabric 28 may be adhered to the adhesion means. Accordingly, if the edge blank portion 23 is widened slightly, the water-flow non-woven fabric 28 can be easily adhered thereto.

The adhesion means may be coated on the top of the partitions 22 and the edge blank portion 23 or the adhesion means may be adhered to the adhesion surface of the water-flow non-woven fabric 28 or a fine perforation resin film using heating adhesion means. Here, the heating adhesion means may include ultrasonic adhesion means or hot-wire heating adhesion means which are chiefly used in the industrial site.

Figure 3:
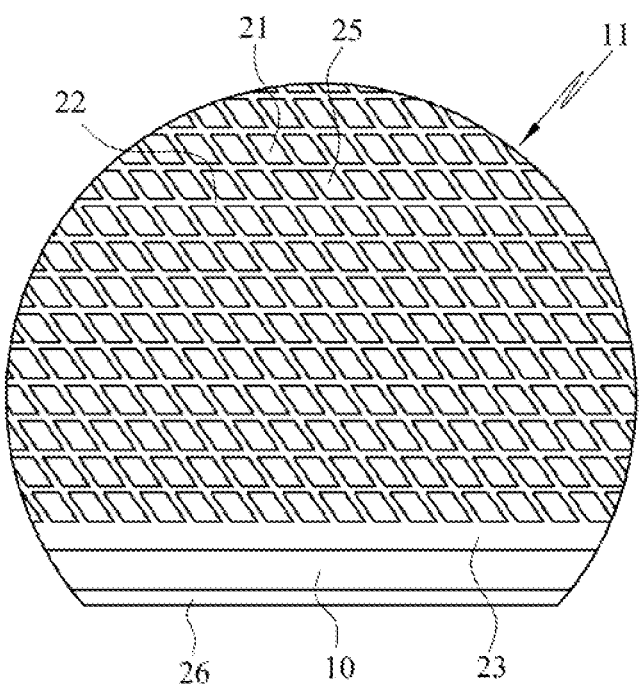
FIG. 3 is a diagram showing fine hole partition means 21 of FIG. 2 including a high suction substance 25.
Figure 4:
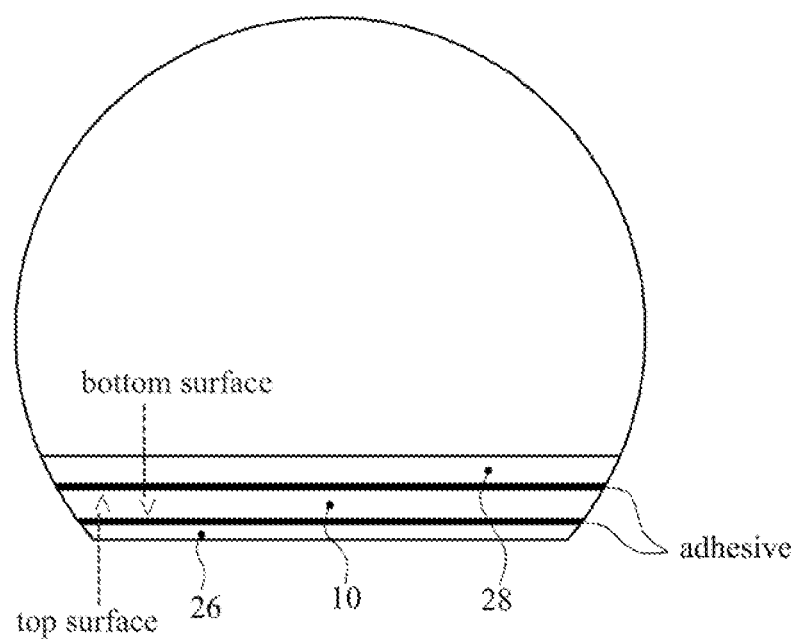
FIG. 4 is a diagram showing the construction of water-flow non-woven fabric 28 in FIG. 3.
Figure 5:
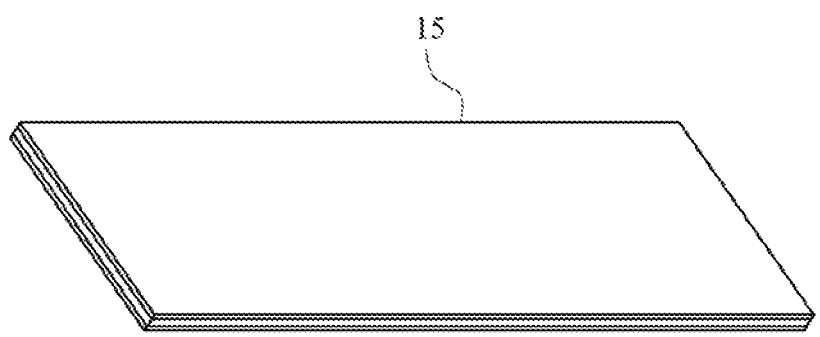
FIG. 5 is a diagram showing of a wrinkle-removing tape 15.

In FIG. 3, the top of the fine hole partition means 21 is open, but the bottom thereof is closed. It is to be noted that the bottom of the fine hole partition means 21 may be perforated if necessary.

A high suction substance 25 is filled in the fine hole partition means 21, and the water-flow non-woven fabric 28 is adhered to the top thereof. High suction resin, high suction polymer, or transparent bead type high suction resin which includes sodium polyacrylate and is capable of absorbing a large amount of moisture, may be used as the high suction substance 25.

In particular, the above resin is applied to diapers or cleaning tools which are commonly seen in the surroundings. The water-flow non-woven fabric 28 can absorb moisture and transmit the moisture toward the high suction substance 25, but the high suction substance 25 does not transmit the moisture or prevents the moisture from being externally protruded when the high suction substance 25 is expanded. The water-flow non-woven fabric 28 may be replaced with the fine perforation resin film or with fine water-flow means of other forms.

In the above construction, it is preferred that the tape means 10, the water-flow non-woven fabric 28, or the fine perforation resin film be transparently fabricated. The tape means 10, the water-flow non-woven fabric 28, or the fine perforation resin film may be fabricated semi-transparently using several colors according to circumstances. The thickness of the partition tape means 10 may be increased if the wrinkles of the skin are large and deep and the thickness of the partition tape means 10 may be decreased if the wrinkles are fine in order to remove wrinkles with various sizes.

What is claimed is:

1. A tape, comprising a plurality of hole partitions, each with an open top, formed on a top surface of the tape made of synthetic resin; a high suction substance filled within the hole partitions; a water-flow film adhered to the top of the hole partitions and the top surface of the tape, the water-flow film is configured to absorb moisture and transmit the moisture to the high suction substance which does not transmit the moisture and prevents the moisture from being externally protruded in response to an expansion of the high suction substance; an adhesive coated on a bottom surface of the tape to adhere the tape to the skin of a human body to remove wrinkles; and a peelable paper to cover the adhesive.

2. The tape of claim 1, wherein the hole partitions are circular hole partitions.

3. The tape of claim 1, wherein the hole partitions are polygonal hole partitions.

4. The tape of claim 1, wherein the synthetic resin is a silicon resin.

5. The tape of claim 1, wherein the synthetic resin is a rubber or latex.

6. The tape of claim 1, wherein the high suction substance comprises sodium polyacrylate.

7. The tape of claim 1, wherein the water-flow film comprises a water-flow non-woven fabric or a perforation resin film.

8. The tape of claim 1, wherein the water-flow film is adhered to an upper part of the tape by an adhesive.

9. A tape, comprising a plurality of hole partitions, each with open top or bottom, formed on a top surface of the tape made of synthetic resin; a high suction substance filled within the hole partitions; a water-flow film adhered to the top of the hole partitions and the top surface of the tape, the water-flow film is configured to absorb moisture and transmit the moisture to the high suction substance which does not transmit the moisture and prevents the moisture from being externally protruded in response to an expansion of the high suction substance; an adhesive coated on a bottom surface of the tape to adhere the tape to the skin of a human body to remove wrinkles and a peelable waterproofing sheet adhered to a bottom surface of the tape to cover the adhesive.

10. The tape of claim 9, wherein the hole partitions are circular hole partitions.

11. The tape of claim 9, wherein the hole partitions are polygonal hole partitions.

12. The tape of claim 9, wherein the synthetic resin is a silicon resin.

13. The tape of claim 9, wherein the synthetic resin is a rubber or latex.

14. The tape of claim 9, wherein the high suction substance comprises sodium polyacrylate.

15. The tape of claim 9, wherein the water-flow film comprises a water-flow non-woven fabric or a fine perforation resin film.

16. The tape of claim 9, wherein the waterproofing sheet comprises a waterproofing synthetic resin film or a rubber film.

17. The tape of claim 9, wherein the water-flow film is adhered to an upper part of the tape by an adhesive.

18. The tape of claim 9, wherein the waterproofing sheet is adhered to a lower part of the tape by an adhesive.

* * * * *